(12) United States Patent
McCants

(10) Patent No.: US 10,207,064 B2
(45) Date of Patent: Feb. 19, 2019

(54) DUAL CHAMBER NEBULIZER APPARATUS

(71) Applicant: Glen McCants, Columbia, SC (US)

(72) Inventor: Glen McCants, Columbia, SC (US)

(*) Notice: Subject to any disclaimer, the term of this patent is extended or adjusted under 35 U.S.C. 154(b) by 0 days.

(21) Appl. No.: 15/646,944

(22) Filed: Jul. 11, 2017

(65) Prior Publication Data
US 2019/0015607 A1    Jan. 17, 2019

(51) Int. Cl.
*A61M 16/00* (2006.01)
*A61M 15/00* (2006.01)
*A61M 11/02* (2006.01)
*A61M 16/14* (2006.01)

(52) U.S. Cl.
CPC ........ *A61M 15/0003* (2014.02); *A61M 11/02* (2013.01); *A61M 15/0005* (2014.02); *A61M 15/009* (2013.01); *A61M 15/0023* (2014.02); *A61M 15/0086* (2013.01); *A61M 16/14* (2013.01)

(58) Field of Classification Search
CPC .............. A61M 15/0003; A61M 16/14; A61M 15/0005; A61M 15/0023; A61M 15/0086; A61M 15/009; A61M 11/02
USPC ...................................... 141/2, 18
See application file for complete search history.

(56) References Cited

U.S. PATENT DOCUMENTS

| | | | |
|---|---|---|---|
| 2,941,696 A * | 6/1960 | Homm .................. | B65D 83/68 128/200.19 |
| 5,287,847 A | 2/1994 | Piper et al. | |
| 7,819,342 B2 | 10/2010 | Spallek et al. | |
| 8,820,321 B2 | 9/2014 | Goede et al. | |
| 9,038,858 B2 | 5/2015 | Hanai et al. | |
| 9,700,117 B2 * | 7/2017 | Dring ..................... | A45D 34/04 |
| 2013/0074842 A1 * | 3/2013 | Boucher ............... | A61M 16/16 128/203.16 |
| 2016/0354558 A1 | 12/2016 | Seguin et al. | |

* cited by examiner

*Primary Examiner* — Steven O Douglas
(74) *Attorney, Agent, or Firm* — Dale J. Ream

(57) ABSTRACT

A dual chamber nebulizer apparatus for atomizing and administering a first and second liquid medicine includes a housing having first and second chambers for holding the first and second liquid medicines. An atomizer member is situated in the housing and configured to atomize liquid into vapor. An air flow member is coupled to the housing and in fluid communication with the atomizer, the flow member having an inlet port for receiving a compressed air flow to the atomizer member. First and second aspiration tubes are in communication with the atomizer member and extend into first and second chambers, respectively. The atomizer member includes a junction in communication with the first and second aspiration tubes, the valve selectively allowing both of the liquid medicines to be drawn through respective aspiration tubes and directed to the atomizer member when the compressed airflow is directed to the atomizer member.

18 Claims, 14 Drawing Sheets

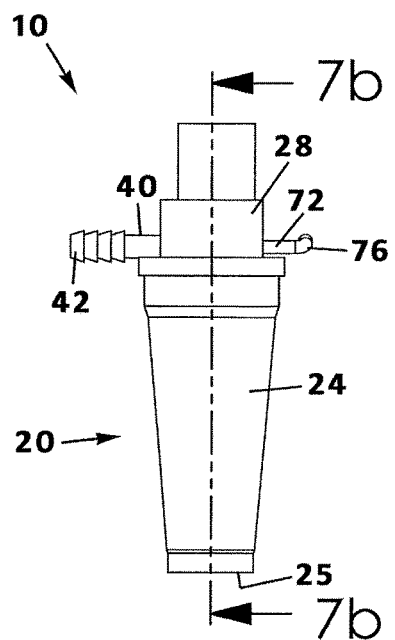
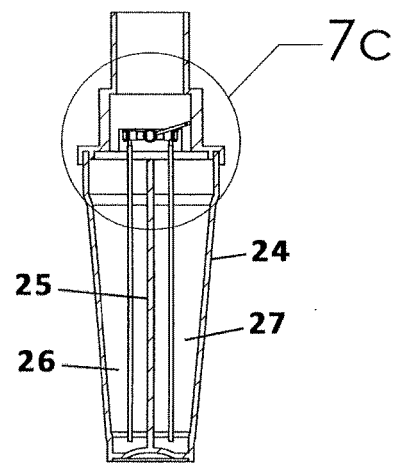
Fig. 7a          Fig. 7b
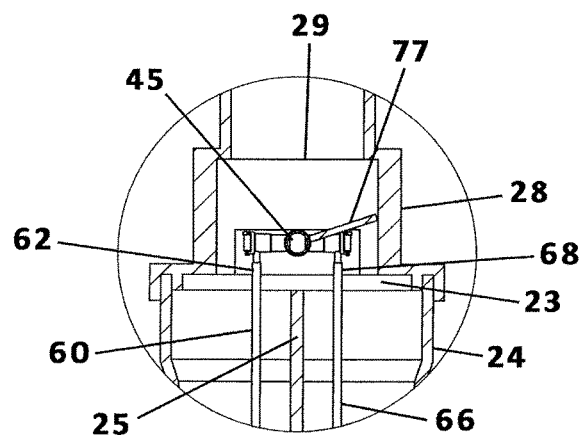
Fig. 7c

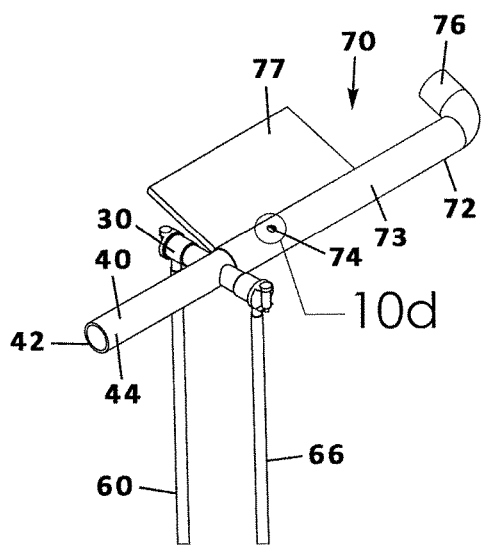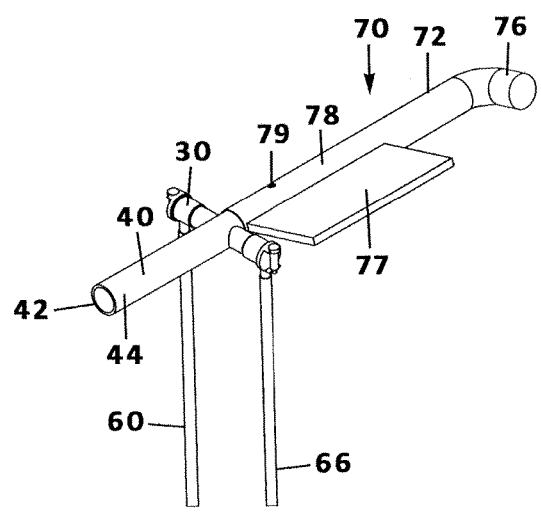
Fig. 10a
Fig. 10b
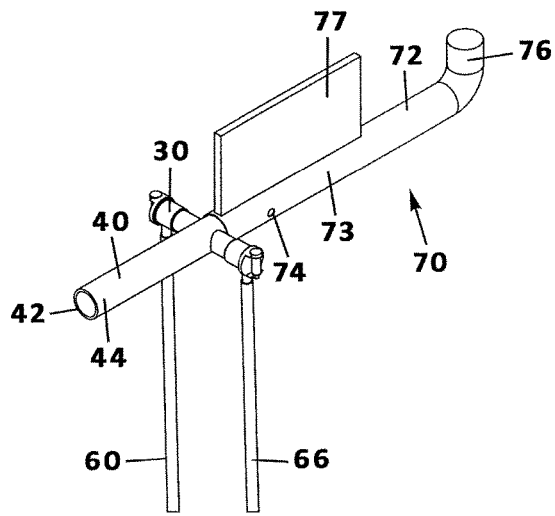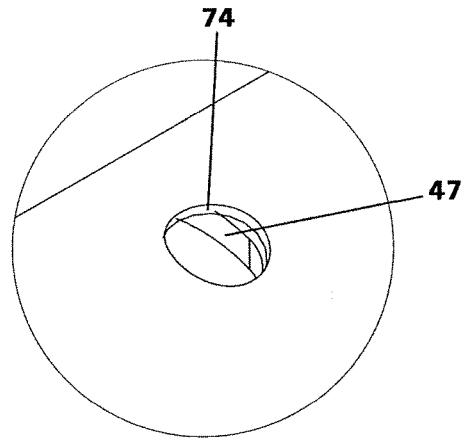
Fig. 10c
Fig. 10d

DUAL CHAMBER NEBULIZER APPARATUS

BACKGROUND OF THE INVENTION

This invention relates to nebulizers for atomizing liquid medicine into medicinal aerosols and, more particularly, to dual chamber nebulizer for selectively atomizing multiple medications simultaneously and providing the atomized medications to a patient.

In the field of respiratory therapy, the primary method of treating patients who suffer from various breathing abnormalities is the use of a small volume nebulizer. The nebulizer is particularly effective because it is capable of delivering medications directly to the lung tissue for immediate absorption. Nebulizers are used to treat a wide array of pulmonary issues ranging from an acute patient who may be experiencing shortness of breath and, as a result, is in need of a rescue medication to a chronic patient who must take inhaled treatments several times per day.

Multiple medications are often required for effective treatment. Currently, the only effective technique for delivering the multiple respiratory medicaments is either to mix them together in the same container or, if the medicaments are incompatible to be mixed, to administer them sequentially (i.e. administer one and then administer the other).

There are many advantages to administering more than one respiratory medicine simultaneously:

- The physical and chemical properties of medication 1 and medication 2 are not compromised as a result of mixing.
- Improved workload efficiency for the caregiver i.e. Respiratory Therapist in the hospital setting "hospitals save money" as simultaneous nebulization takes less time.
- Improved patient tolerance as a result of less time for nebulization to occur; in particular, children with cystic fibrosis require multiple medications for effective treatment. Children are impatient for wearing a mask over their face as they are by nature somewhat claustrophobic. The primary nebulized medication for treating cystic fibrosis is Pulmozyme. Pulmozyme is essentially incompatible with all other nebulized medications which are indicated for treatment".
- Eliminates the visual incompatibility issue as there are instances where the drug manufacturers may not list a certain medication as incompatible with another, but when mixed in the liquid state and nebulized it is obvious to the respiratory therapist that they foam up which results in a much less efficient nebulization process".
- Eliminates the need for costly and protracted research studies. There are many medications that fall into a category where there is incomplete research or no research at all to confirm compatibility.
- Hospitals save money as the need to purchase two or more nebulizers can be replaced with purchasing one.
- Individuals save money as the need to purchase two or more nebulizers can be replaced with purchasing one in the home setting.

Therefore, it would be desirable have a dual chamber nebulizer apparatus capable of holding two liquid medications and which can be simultaneously atomized into vapor and administered through a mouthpiece. Further, it would be desirable to have a dual chamber nebulizer apparatus having a delivery member having a flexible neck that maintains the nebulizer in an upright orientation even when the patient is completely recumbent and lying with his head to the left or right.

SUMMARY OF THE INVENTION

A dual chamber nebulizer apparatus for atomizing a first and second liquid medicine and for administering the atomized medicine according to the present invention includes a housing having a first chamber for holding the first liquid medicine and a second chamber for holding the second liquid medicine, the first chamber being structurally separated from the second chamber. An atomizer member is situated in an upper portion of the housing that is configured to atomize liquid into vapor. An air flow member is coupled to the housing and in fluid communication with the atomizer member, the flow member having an inlet port selectively receiving and directing a compressed air flow to the atomizer member.

The present apparatus may include a refill assembly having a ramp member selectively positioned to guide a liquid medicine into a selected chamber while blocking its entry into the other chamber.

First and second aspiration tubes are in fluid communication with the atomizer member and extend downwardly into first and second chamber, respectively, the aspiration tubes being perpendicular to the atomizer member. The atomizer member, flow member, and the aspiration tubes together form a junction that is operable to selectively allow one or both of the first and second liquid medicines to be drawn through the first and second aspiration tubes, respectively, to the atomizer member when the compressed airflow is also directed to the atomizer member to atomize the medicines and deliver them to the delivery device.

Therefore, a general object of this invention is to provide a dual chamber nebulizer apparatus for atomizing and delivering multiple respiratory medications simultaneously.

Another object of this invention is to provide a dual chamber nebulizer apparatus, as aforesaid, that includes a housing having first and second medicine chambers separate by a barrier well to prevent the medicines from mixing until simultaneously atomized and inhaled.

Still another object of this invention is to provide a dual chamber nebulizer apparatus, as aforesaid, that includes a delivery assembly having a flexible tubing configured to bend in any lateral direction so that the apparatus may be used by a recumbent patient even if the patient's head is turned to the left or right.

Yet another object of this invention is to provide a dual chamber nebulizer apparatus, as aforesaid, having a pivotal loading ramp for directing liquid medicine into a selected first or second medicine chamber.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1 is a perspective view of a dual chamber nebulizer according to a preferred embodiment of the present invention, illustrated with a delivery member in a linear configuration;

FIG. 2 is a perspective view of the dual chamber nebulizer as in FIG. 1, illustrated with the delivery member in a partially bent configuration;

FIG. 3 is a perspective view of the dual chamber nebulizer as in FIG. 1, illustrated with the delivery member in a completely bent configuration;

FIG. 7a is a front view of the nebulizer apparatus as in FIG. 1;

FIG. 7b is a sectional view taken along line 7b-7b of FIG. 7a illustrated with a loading ramp pivoted to direct refilled liquid medicine into the first medicine chamber;

FIG. 7c is an isolated view on an enlarged scale taken from FIG. 7b;

FIG. 9b is a sectional view taken along line 9b-9b of FIG. 9a;

FIG. 10a is a perspective view of the junction assembly and refill assembly removed from the housing illustrated with the loading ramp pivoted to direct refilled liquid medicine into the one medicine chamber;

FIG. 10b is a perspective view of the junction assembly and refill assembly removed from the housing illustrated with the loading ramp pivoted to direct refilled liquid medicine into another medicine chamber;

FIG. 10c is a perspective view of the junction assembly and refill assembly removed from the housing illustrated with the loading ramp pivoted to an upright operational position;

FIG. 10d is an isolated view on an enlarged scale taken from FIG. 10a;

FIG. 11a is an exploded view of the junction assembly and refilling assembly as in FIG. 10a;

FIG. 11b is an isolated view on an enlarged scale taken from FIG. 10a;

FIG. 13b is a sectional view taken along line 13b-13b of FIG. 13a;

FIG. 14b is a sectional view taken along line 14b-14b of FIG. 14a.

DESCRIPTION OF THE PREFERRED EMBODIMENT

Figure 1:
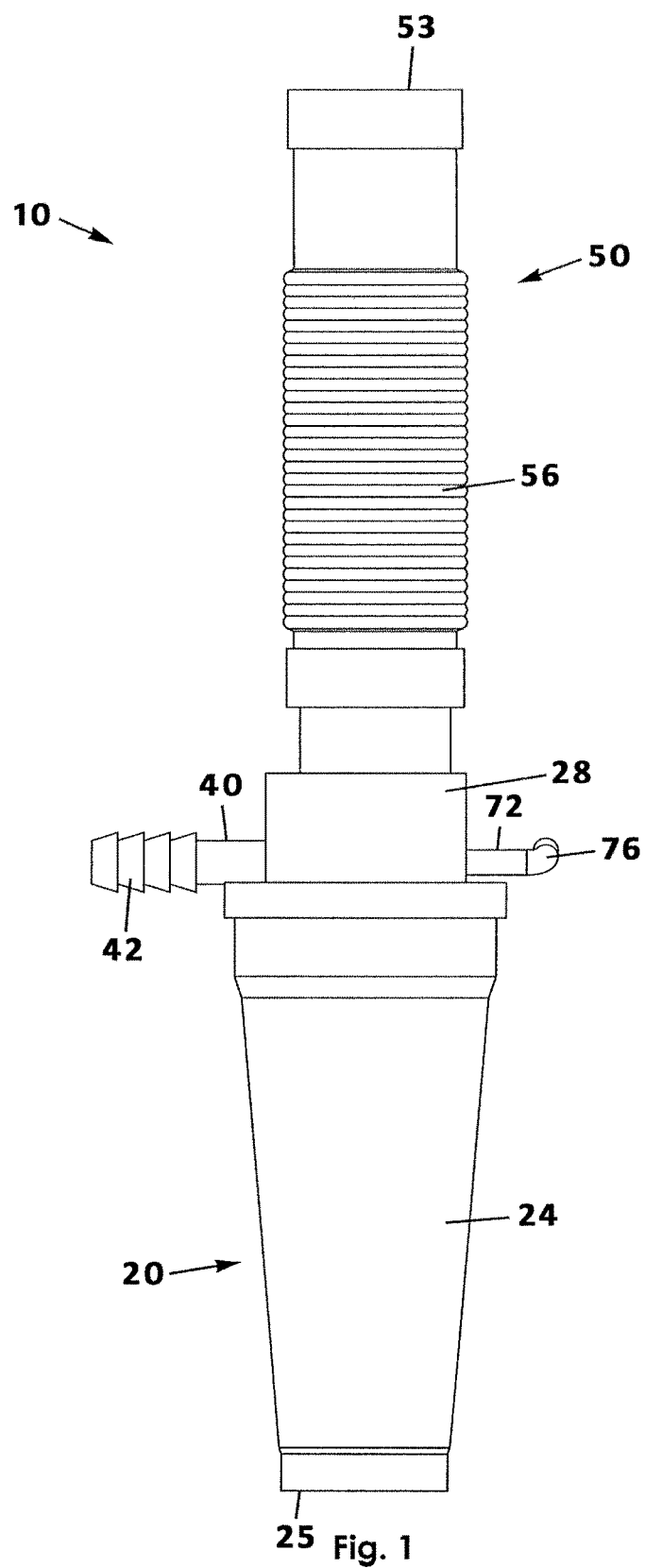
Figure 2:
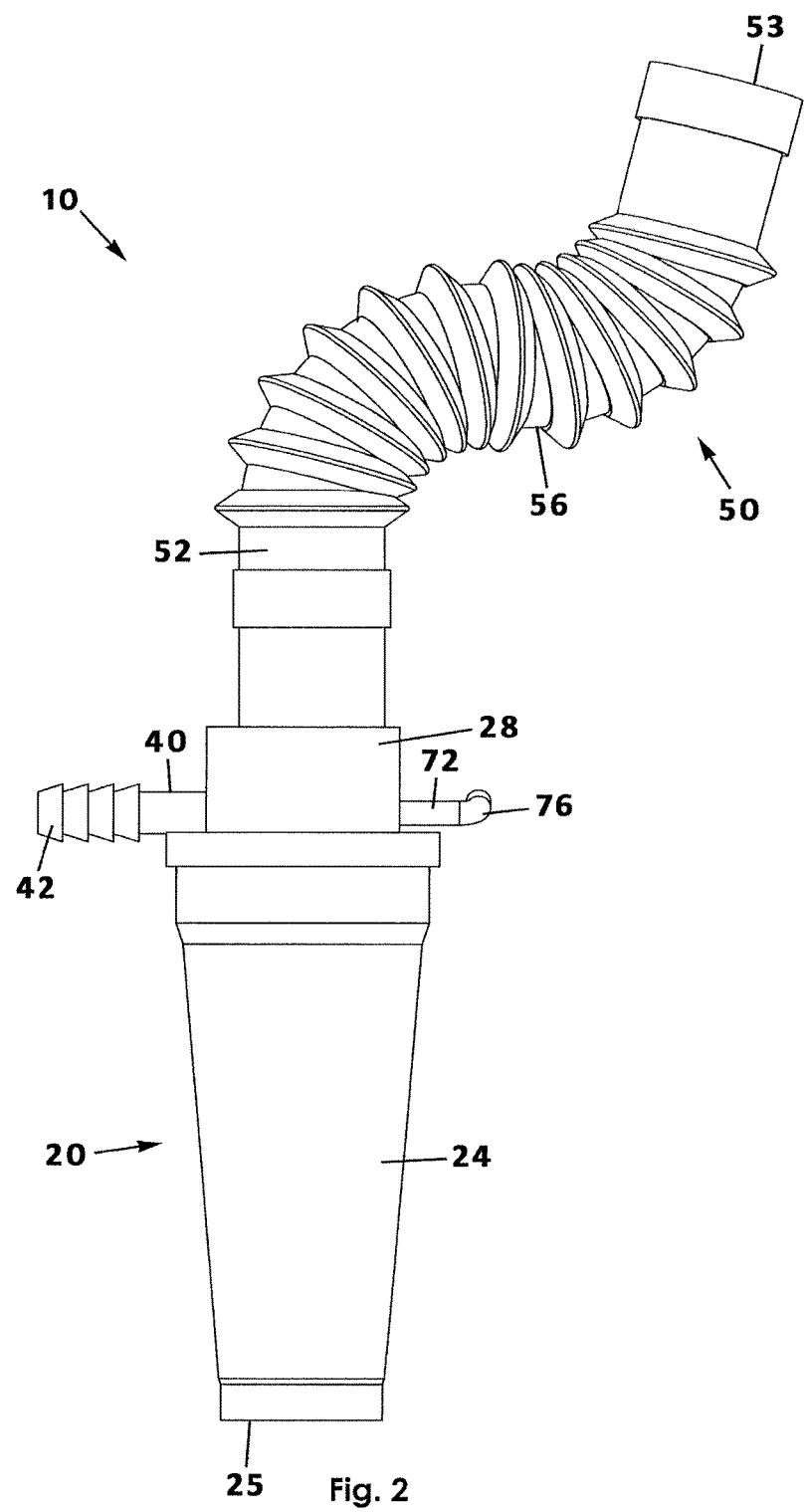
Figure 3:
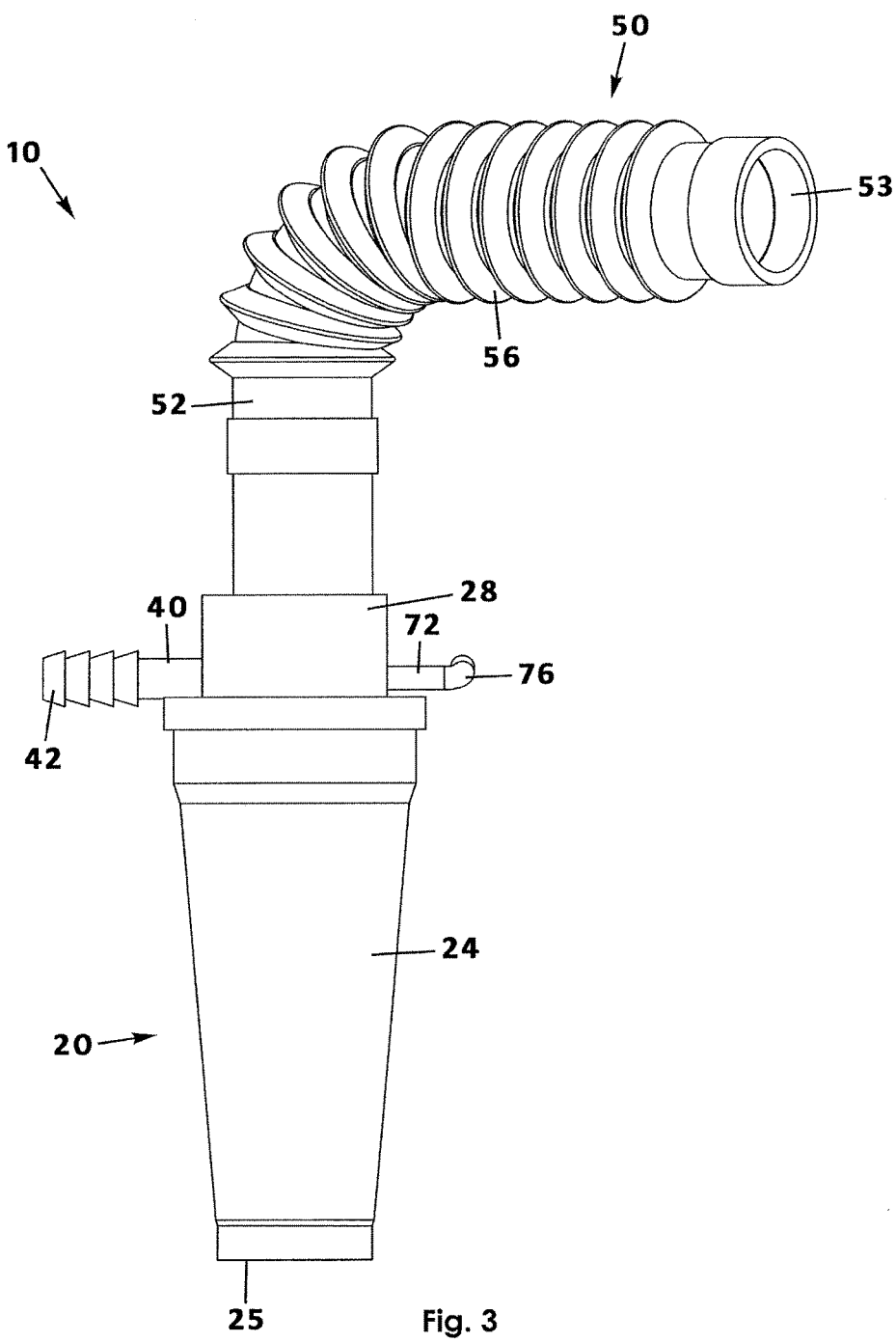
Figures 4A, 4B:
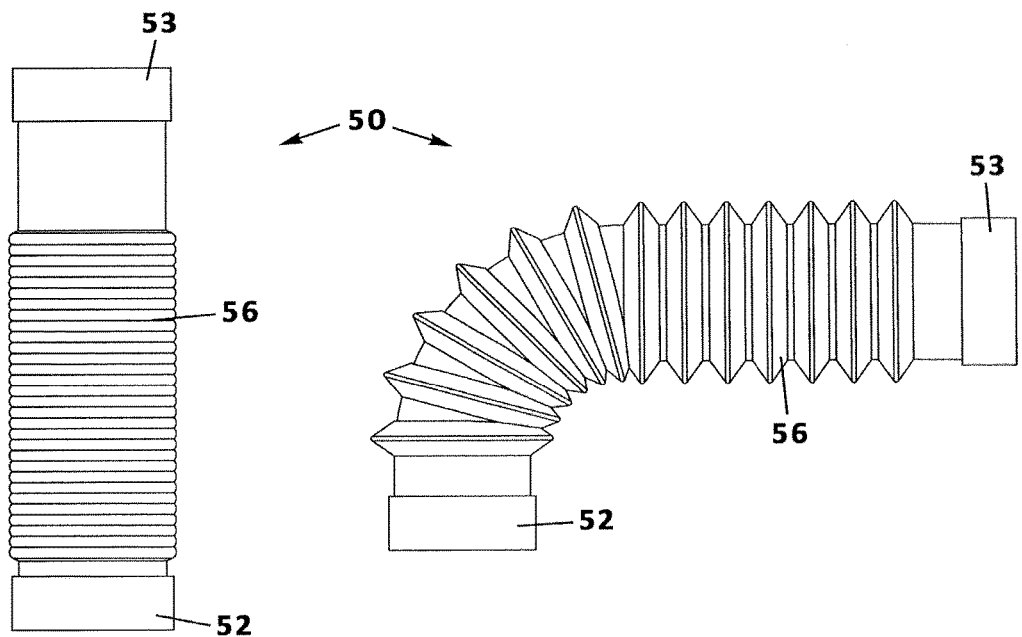
FIG. 4a is a side view of the delivery member removed from the dual chamber nebulizer illustrated in a linear configuration.
FIG. 4b is another side view of the delivery member as in FIG. 4a illustrated in a full bent configuration.
Figure 4C:
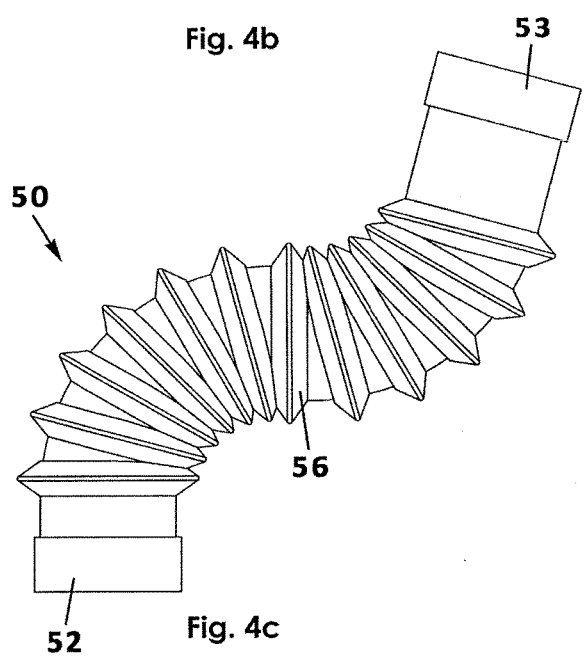
FIG. 4c is another side view of the delivery member as in FIG. 4a illustrated in a multiple bent configuration.
Figures 5, 6:
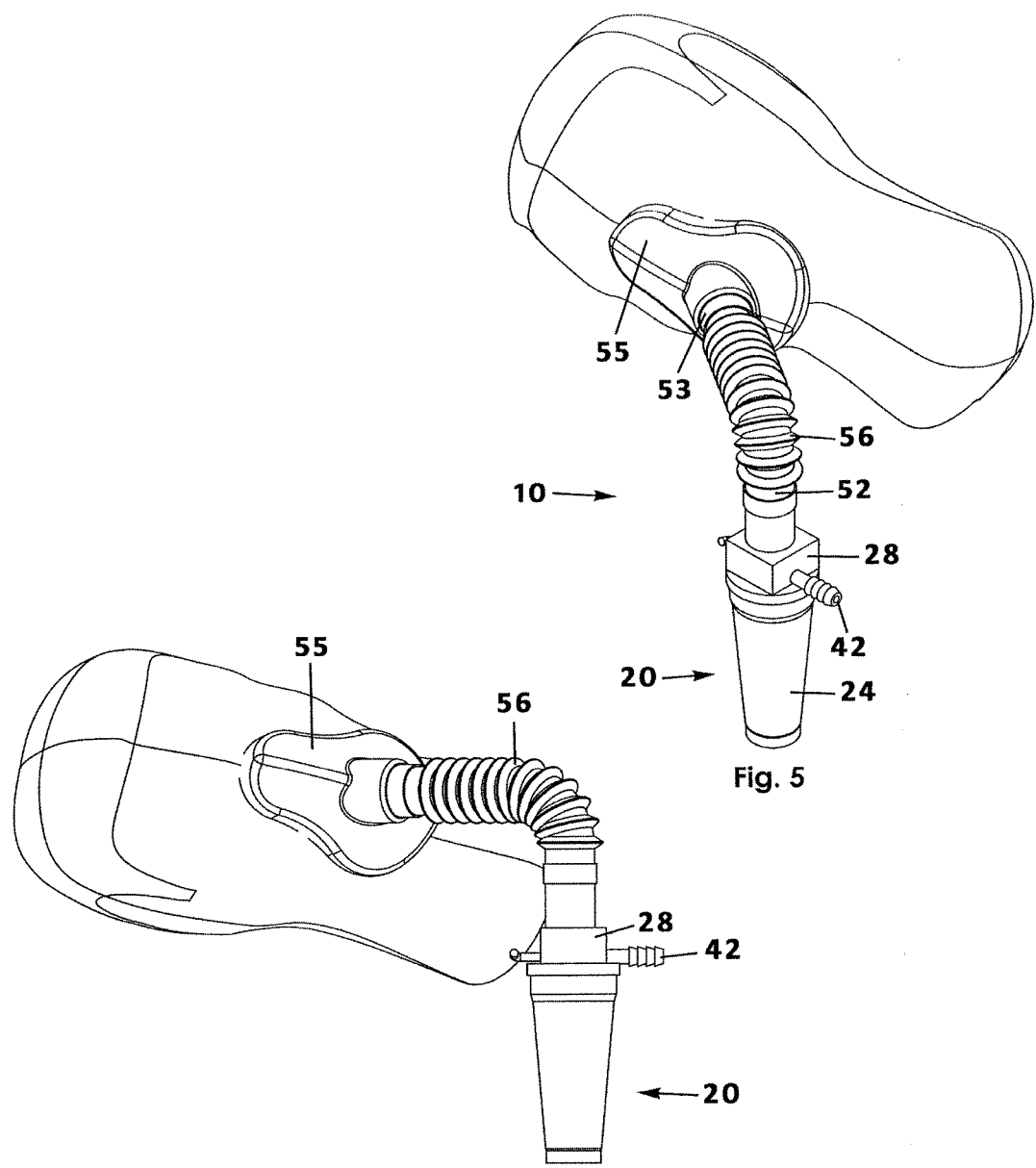
FIG. 5 is a perspective view of the nebulizer as in FIG. 1 in use with a patient lying in one orientation.
FIG. 6 is a perspective view of the nebulizer as in FIG. 1 in use with a patient lying in a different orientation.
Figure 8A:
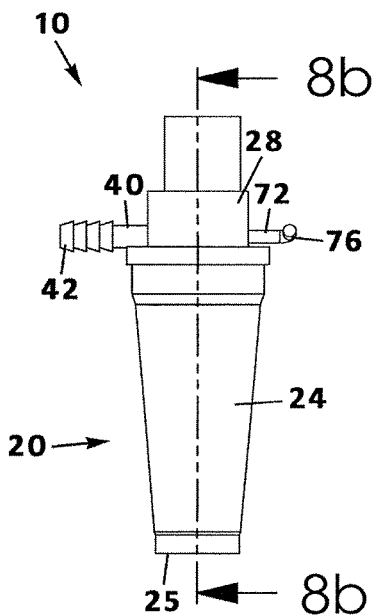
FIG. 8a is a front view of the nebulizer apparatus as in FIG. 1.
Figure 8B:
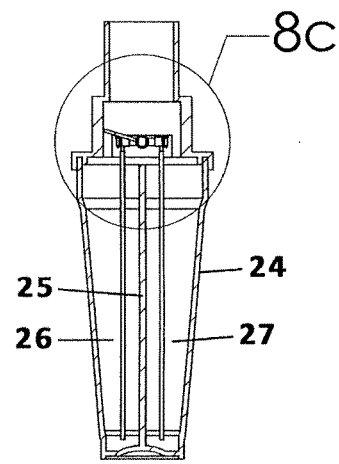
FIG. 8b is a sectional view taken along line 8b-8b of FIG. 8a illustrated with the loading ramp pivoted to direct refilled liquid medicine into the second medicine chamber.
Figure 8C:
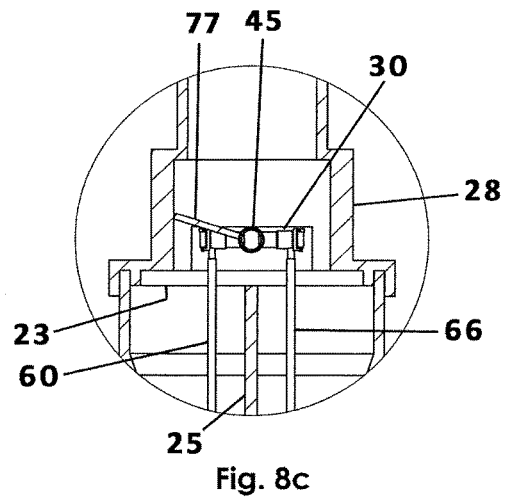
FIG. 8c is an isolated view on an enlarged scale taken from FIG. 8b.
Figure 9A:
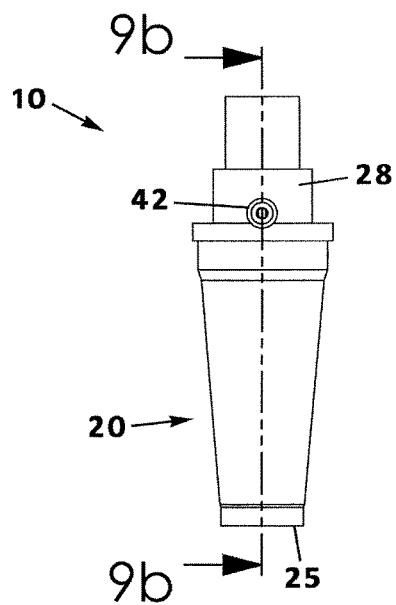
FIG. 9a is a front view of the nebulizer apparatus as in FIG. 1.
Figure 9B:
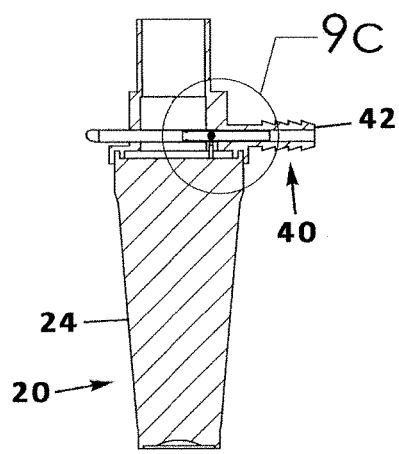
Figure 9C:
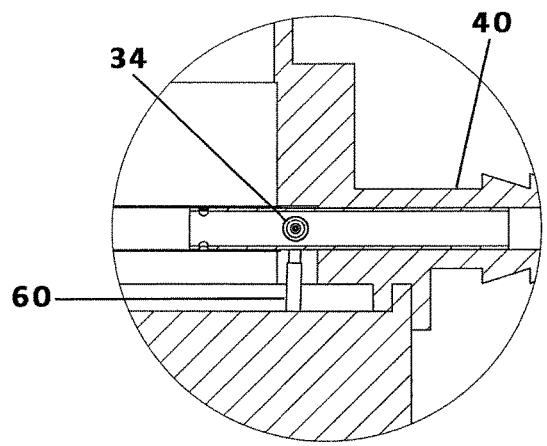
FIG. 9c is an isolated view on an enlarged scale taken from FIG. 9b.

A dual chamber nebulizer apparatus according to a preferred embodiment of the present invention will now be described with reference to FIG. 1-14b of the accompanying drawings. The dual chamber nebulizer apparatus 10 includes a housing 20, an atomizer member 30, a flow member 40, aspiration tubes for drawing liquid medicine from corresponding medicine chambers 26, 27, and a delivery member 50 of atomized medicine to a patient.

The housing 20 provides reservoirs for holding liquid medicine to be atomized and delivered to a nebulizer patient as well as containing other components of the nebulizer apparatus 10. The housing 20 may include a bottom wall 22 or base suitable to support the housing 20 on a flat surface. The housing 20 includes a continuous side wall 24 extending upwardly from the bottom wall 22 such that the housing includes a cylindrical configuration defining a generally hollow interior space. The housing may include a top wall 23 opposite the bottom wall 22 although the top wall 23 may be partial as it still gives access to an interior area of the housing 20 as will be described later. Preferably, a barrier wall 25 extends upwardly from the bottom wall 22 an equal distance between the peripheral edges of the side wall 24 such that two chambers are formed for containing and separating two liquid medicines. More particularly, the continuous side wall 24 and barrier wall 25 define a first chamber 26 and a second chamber 27 each defining an open top wherein to receive first and second liquid medicines, respectively, as will be described in more detail later.

The housing 20 includes an upper housing portion 28 coupled to upper ends of the continuous side wall 24 and defines an open area therein (FIG. 7c). In an embodiment, the upper housing portion 28 may be releasably or removably coupled to the continuous side wall 24, such as in a rotatable or friction fit engagement. An atomizer member 30 is situated in the open area of the upper housing portion 28 and has a generally tubular construction. More particularly, the atomizer member 30 has a pair of opposed ends 32. Each opposed end 32 has a closed configuration except that it defines a small diameter channel 34 through which air is allowed to pass. The atomizer member 30 includes a pair of baffles 36, each baffle 36 positioned external of each closed end 32, respectively, and slightly displaced outwardly from a corresponding closed end 32. Each baffle 36 has a solid construction that substantially blocks atomized air exiting the atomizer member 30 via a channel 34, respectively, and simply redirects the atomized air to pass out the open 29 of the upper housing portion 28 and into the delivery member 50 as shown by the arrows in FIG. 13b).

Figure 11A:
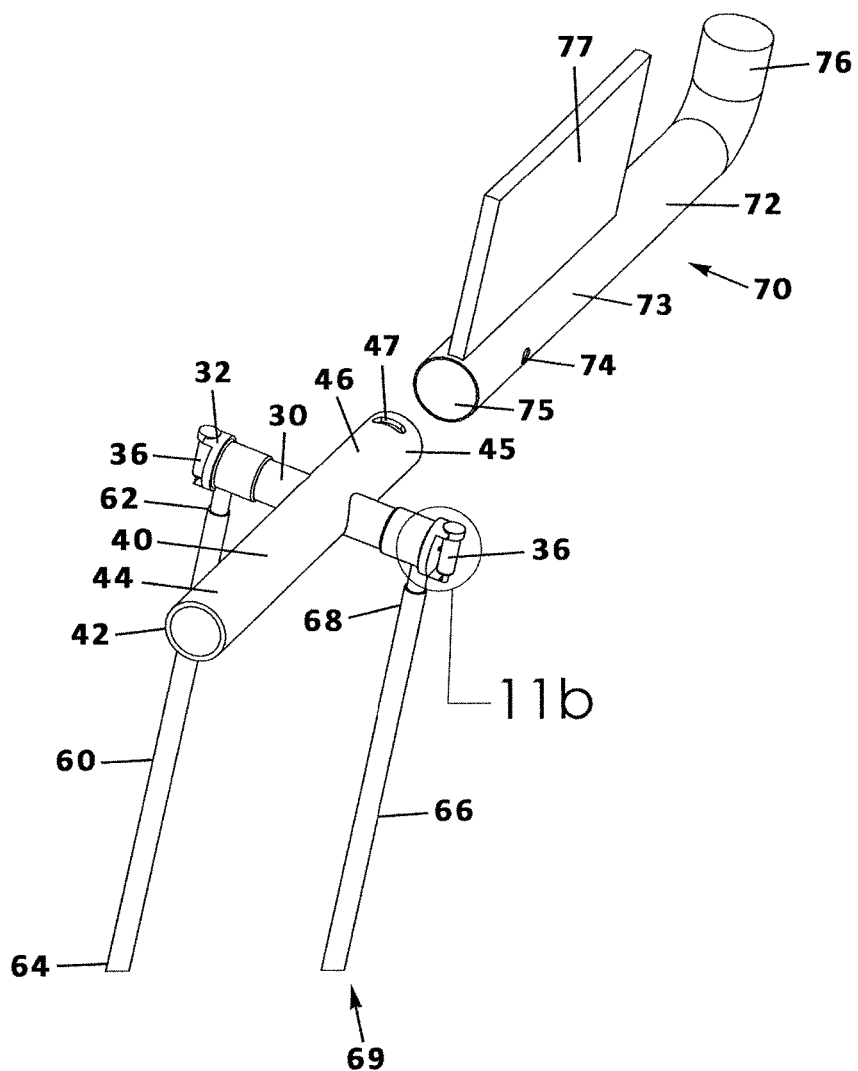
Figure 11B:
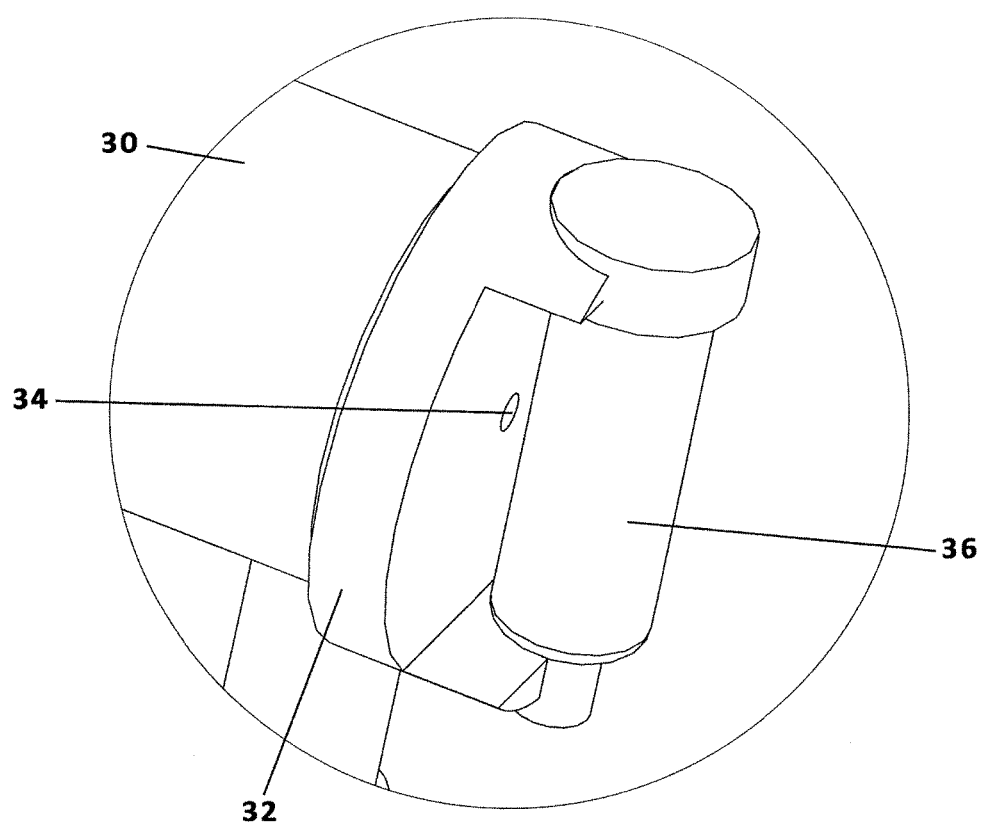
Figure 12:
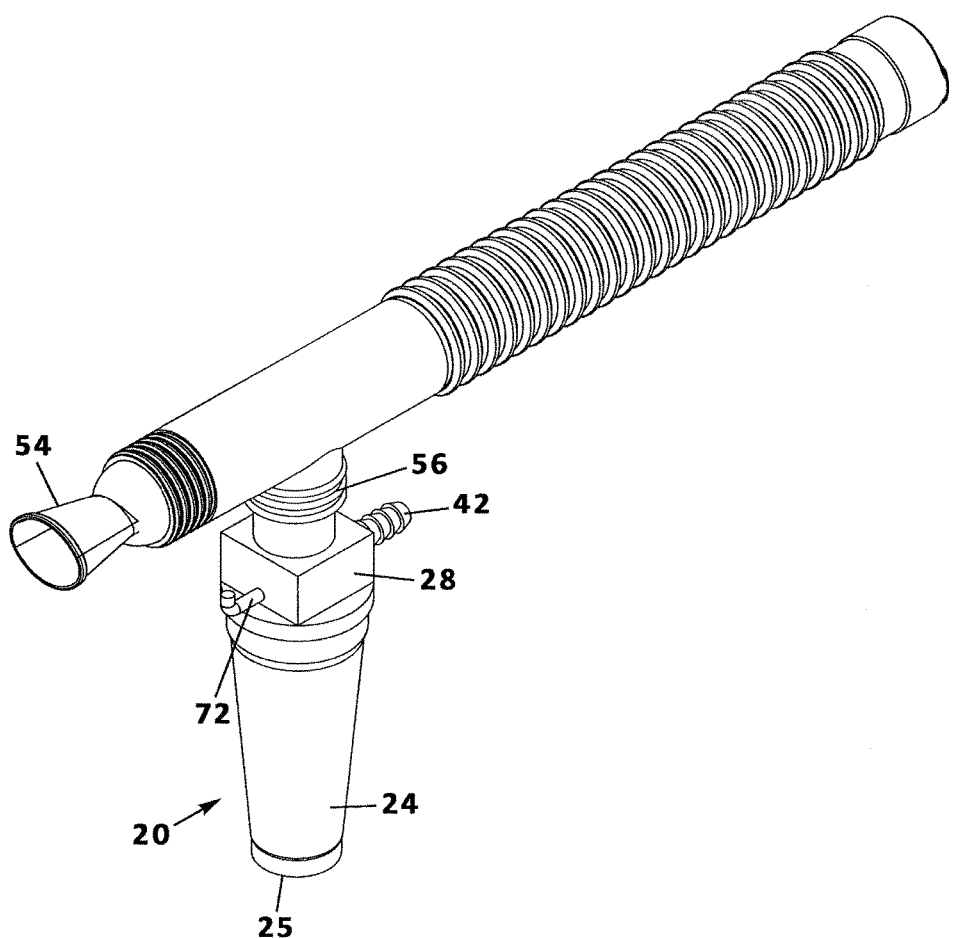
FIG. 12 is a perspective view of a dual chamber nebulizer according to a preferred embodiment of the present invention, illustrated with a delivery member in a linear configuration.
Figure 13A:
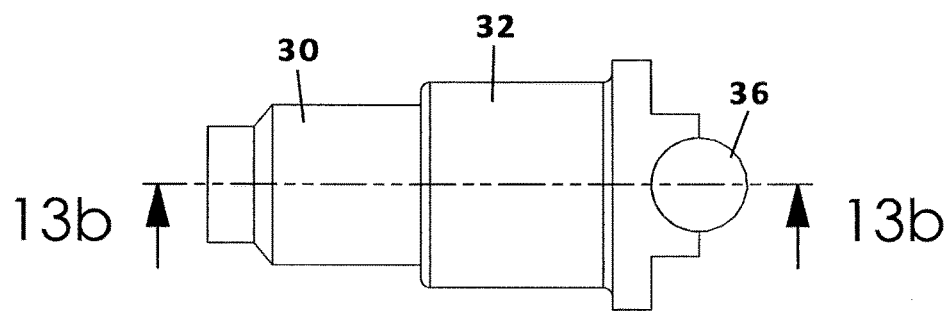
FIG. 13a is a perspective view of the flow member removed from the housing of FIG. 1.
Figure 13B:
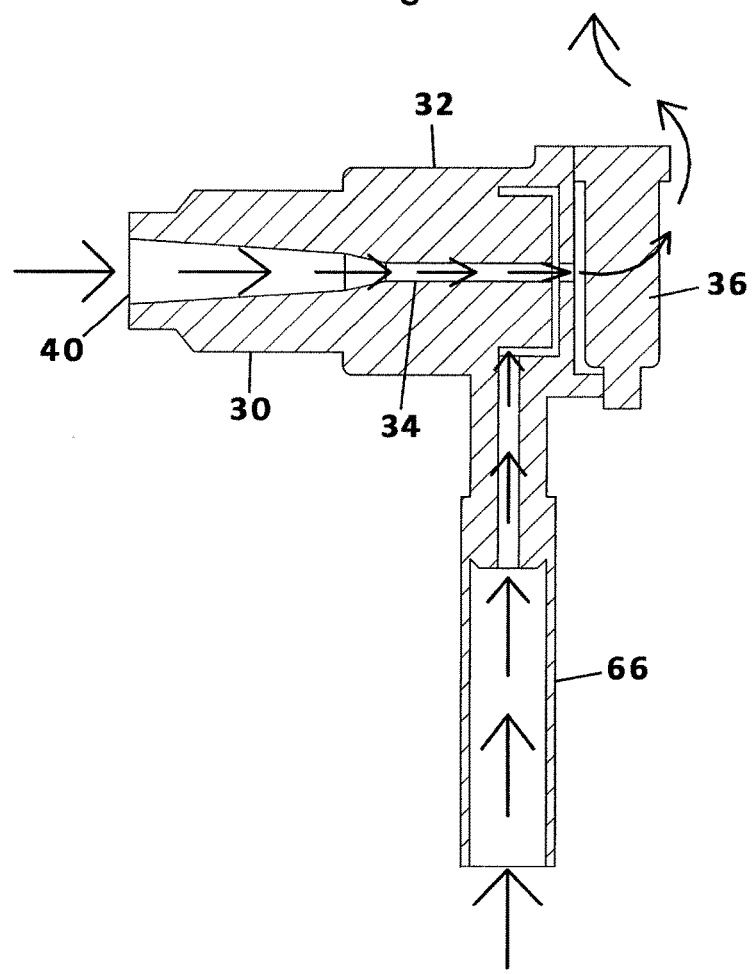
Figure 14A:
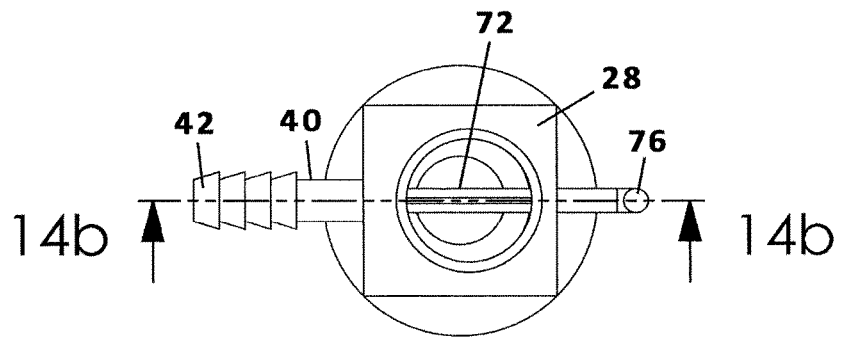
FIG. 14a is a top view of the dual chamber nebulizer as in FIG. 1.
Figure 14B:
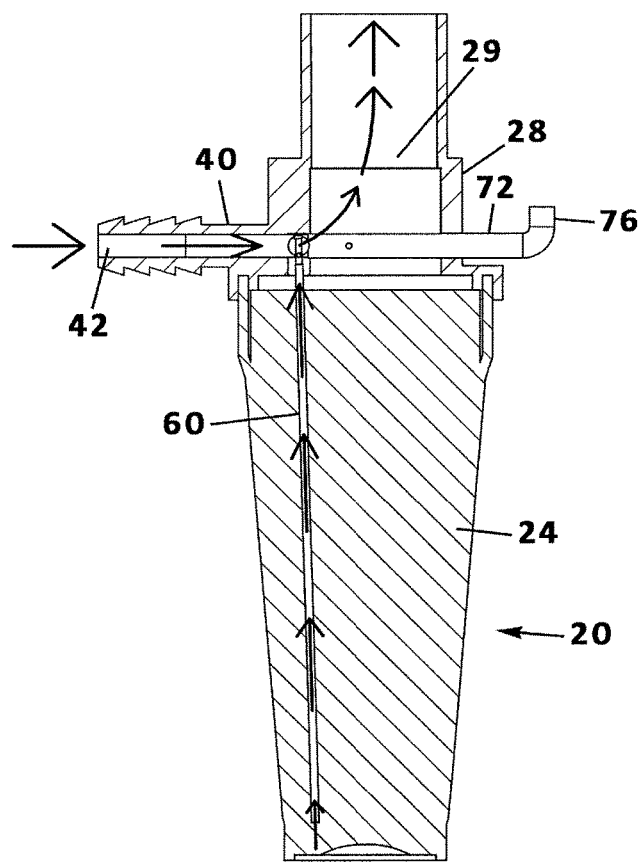

The flow member 40 is connected to the upper housing portion 28 of the housing 20, has a tubular configuration, and includes an inlet port 42 for connection to a high pressure airflow, e.g. a compressor or similar medical device (not shown), the flow member 40 being coupled to the atomizer member 30 and in fluid communication therewith (FIG. 11a). It is understood that the high speed air stream is directed into the tubular atomizer member 30 by the flow member 40 such that the air stream is then directed toward the closed ends 32 therein. The flow member 40 includes a proximal end 44 external of the upper housing portion 28 to which the input port 42 is attached. The flow member 40 includes a distal end 45 opposed to the proximal end 44, the distal end 45 having a top wall 46 that defines an aperture 47. This aperture 47 will either be aligned with an air hole defined by the refill assembly 70, an alignment resulting in non-operation of the nebulizer apparatus or alignment resulting in non-operation, as will be described later. It is understood that the flow member 40 and the atomizer member 30 may have a singular or integrated construction and may, collectively, define what is referred to as a T-valve.

The dual chamber nebulizer apparatus 10 includes a first aspiration tube 60 having a proximal end 62 coupled to and in fluid communication with the atomizer member 30 and having a distal end 64 extending into the first chamber 26. Liquid medicine in the first chamber 26 is drawn through the first aspiration tube 60 by the operation of the high speed air stream being urged into the atomizer member. The combination of the high speed air stream and drawn up liquid medicine results in atomization of the liquid medicine which is then pushed through a respective closed end channel 34.

Similarly, the dual chamber nebulizer apparatus 10 includes a second aspiration tube 66 having a proximal end 68 coupled to and in fluid communication with the atomizer member 30 and having a distal end 69 extending into the second chamber 27. Liquid medicine in the second chamber 27 is drawn through the second aspiration tube 66 by the operation of the high speed air stream being urged into the atomizer member. The atomizer member, flow member, and the aspiration tubes together form a junction that is operable to selectively allow one or both of the first and second liquid medicines to be drawn through the first and second aspiration tubes, respectively, to the atomizer member when the compressed airflow is also directed to the atomizer member to atomize the medicines and deliver them to the delivery device. The combination of the high speed air stream and drawn up liquid medicine results in atomization of the liquid medicine which is then pushed through a respective closed end channel 34.

In another aspect, the dual chamber nebulizer apparatus 10 includes a delivery member 50 that directs atomized medicine from the atomizer member 30 to a patient. In an embodiment, the delivery member includes an open proximal end 52 releasably coupled to an upper end of the upper housing portion 28 of the housing 20, the delivery member 50 being in fluid communication with atomized medicines (first and second liquid medicines) being released by the atomizer member 30 as described above. An open distal end 53 opposite the open proximal end 52 includes an outlet port configured to deliver atomized medicine to a patient who may inhale it directly from a mouthpiece 54 coupled to the open distal end 53 (FIG. 13) or via a mask 55 coupled to the open distal end 53 (FIGS. 5 and 6).

Advantageously, the delivery member 50 is constructed of flexible tubing 56 that may be bent, shaped, and directed in virtually any direction as shown in FIGS. 4*a* to 4*c* (i.e. to the left, right, forward, rearward). Further, the delivery member 50 may be flexible plastic tubing having a plurality of pleated coil sections that are bendable and length adjustable. It is understood that the flexibility of the delivery member 50 enables the dual chamber nebulizer apparatus 10 to be administered and used regardless if a recumbent patient's head is oriented to the left, to the right, or facing upwardly while, in all cases, the housing 20 remains upright or upstanding and level (FIGS. 5 and 6).

In another aspect, the dual chamber nebulizer apparatus 10 includes a refill assembly 70 so that the first 26 and second 27 chambers of the housing 20 may be quickly, accurately, and cleanly refilled. The refill assembly 70 includes a body portion 72 having a tubular configuration extending between an inner end 75 coupled to the distal end 45 of the flow member 40 and an outer end 76 opposite and displaced from the inner end 75. The inner end 75 is situated inside the upper housing portion 28 and the outer end 76 is situated outside the upper housing portion 28. The body portion 72 of the refill assembly 70 is essentially a sleeve defining an interior space and the inner end 75 is open. Accordingly, the sleeve is configured to receive the distal end 45 of the flow member 40—distal end first—in a nested relationship such that the body portion 72 is rotatable relative to the flow member 40 as will be described below. The outer end 76 of the refill assembly 70 is perpendicular to the body portion 72 such that the body portion 72 and outer end 76, when viewed together, have an L-shaped configuration. The outer end 76 has a tactile configuration that may be gripped by a user's fingers during the filling process to be described below.

Further, the refill assembly 70 includes a ramp member 77 coupled to the body portion 72 adjacent the inner end 75 of the refill assembly 70, the ramp member 77 having a planar configuration extending away from the body portion 72 (FIG. 11*a*). The edge of the ramp member 77 coupled to the body portion 72 is such that the ramp member 77 is perpendicular to the body portion 72 and extends away therefrom. The ramp member is generally flat and operates to allow a first liquid medicine to flow into the first chamber 26 and a second liquid medicine to flow into the second chamber 27, depending on which direction the body portion 72 and ramp member 77 are rotated. More particularly, the ramp member 77 may be rotated (by rotating the body portion 72 via gripping the outer end 76) to a first refill configuration covering the open top of the second chamber 27 (allowing access only to the first chamber 26) and a second refill configuration covering the open top of the first chamber 26 (allowing access only to the second chamber 27). Further, the ramp member 77 may be rotated to an operational configuration allowing access to both first 26 and second 27 chambers. It is understood that when the delivery member 50 is released and removed from the upper housing portion and the ramp member 77 is rotated to cover and block access to one chamber, a liquid medicine may be poured or injected through the open tops of respective upper housing portion 28 and uncovered chamber (FIGS. 7*c* and 8*c*).

Operation of the dual chamber nebulizer apparatus 10 is possible only when the refill assembly 70 and, more particularly, the ramp member 77 is rotated to an upstanding or vertical configuration (FIG. 10*c*). More particularly, atomization of the two liquid medicines can only occur when the high speed air stream is passed from the flow member 40 to the atomizer member 30 and the atomization member is a closed environment with no air leakage other than the channels 34 at opposed closed ends 32 as described above. The following description explains the structure by which this environment is created and regulated.

The body portion 72 of the refill assembly 70 defines a first side wall 73 defining a first air hole 74. In like manner, the body portion 72 of the refill assembly 70 defines a second side wall 78 defining a second air hole 79. And, as described previously, the flow member 40 defines an aperture 47 adjacent a distal end 45 thereof. The ramp member 77 is positioned between the first air hole 74 and second air hole 79. The first air hole 74, second air hole 79, and aperture 47 are positioned to be selectively aligned when the body portion 72 is appropriately rotated. Specifically, the first air hole 74 and aperture 47 become aligned (also described as being "registered") when the refill assembly 70 is at the first refill configuration and the second air hole 79 and aperture 47 become aligned when the refill assembly 70 is at the second refill configuration. In both cases, the air stream delivered to the atomizer member 30 by the flow member 40 is allowed to escape through respective aligned aperture and air holes and, as a result, no atomization occurs and the nebulizer apparatus 10 does not function. In an embodiment, the first air hole 74 and second air hold 79 may be cut in such a way to emit an audible whistle when air passes therethrough. As alternative to a whistle sound, other audible sounds may be used that indicates to a user that the refill assembly 70 is positioned in a manner that is not airtight and is not functional. However, when the ramp member 77 is in the upright configuration, the aperture 47 is not aligned with either air hole and the requisite closed environment is maintained and the nebulizer apparatus 10 is allowed to function.

It is understood that while certain forms of this invention have been illustrated and described, it is not limited thereto except insofar as such limitations are included in the following claims and allowable functional equivalents thereof.

The invention claimed is:

1. A dual chamber nebulizer apparatus for atomizing a first and second liquid medicine and for administering the atomized medicine, comprising:

a housing having a first chamber for holding the first liquid medicine and a second chamber for holding the second liquid medicine, said housing having a barrier wall that separates said first chamber from said second chamber;

an atomizer member situated in an upper portion of said housing and configured to atomize liquid into vapor;

a flow member coupled to said housing and in fluid communication with said atomizer member, said flow member having an inlet port selectively directing a compressed air flow to said atomizer member;

a first aspiration tube having a proximal end in fluid communication with said atomizer member and a distal end extending into said first chamber, said first aspiration tube being perpendicular to said atomizer member;

a second aspiration tube having a proximal end in fluid communication with said atomizer member and a distal end extending into said second chamber, said second aspiration tube being perpendicular to said atomizer member;

wherein said atomizer member, said flow member, and said first and second aspiration tubes collectively form a junction that is operable to draw the first and second liquid medicines from said first and second medicine chambers via said first and second aspiration tubes, respectively, into said atomizer member where the compressed air flow atomizes the first and second liquid medicines;

a delivery member having a proximal end coupled to an upper end of said housing and in fluid communication with said atomizer member for receiving said atomized first and second medicines and a distal end displaced from said housing;

wherein said delivery member includes an outlet port situated at said distal end;

wherein said delivery member is constructed of flexible tubing that is selectively shaped to extend away from said housing in any direction.

2. The nebulizer apparatus as in claim 1, wherein said delivery member is length adjustable.

3. The nebulizer apparatus as in claim 2, wherein said delivery member is constructed of flexible plastic tubing having a plurality of pleated coil sections.

4. The nebulizer apparatus as in claim 1, wherein said housing includes:

a bottom wall;

a top wall opposite the bottom wall;

a continuous side wall extending between peripheral edges of said bottom and top walls, respectively, said bottom, top, and continuous side wall collectively defining an interior space;

wherein said barrier wall is positioned in said interior space of said housing and extends between said bottom wall and said top wall, said barrier wall being displaced from said continuous side wall to separate said first chamber from said second chamber.

5. The nebulizer apparatus as in claim 1, further comprising a refill assembly having an inner end coupled to a distal end of said flow member and an outer end opposite said inner end and situated outside of said housing, said refill assembly including a body portion having a tubular configuration and extending between said inner and outer ends.

6. The nebulizer apparatus as in claim 5, wherein:

said refill assembly includes a ramp member coupled to said body portion of said ramp assembly, said ramp member having a planar configuration;

said inner end of said refill assembly is rotatably coupled to said distal end of said flow member so that said refill member is rotatable between a first refill configuration allowing access only to said first chamber and a second refill configuration allowing access only to said second chamber and an operational configuration allowing access to both first and second chambers.

7. The nebulizer apparatus as in claim 6, wherein:

said ramp member covers an open top defined by said second chamber when said ramp member is at said first configuration and said ramp member covers an open top defined by said first chamber when said ramp member is at said second configuration.

8. The nebulizer apparatus as in claim 5, wherein:

said body portion of said refill assembly is a sleeve defining an interior space that selectively receives said distal end of said flow member in a rotatably nested configuration;

said outer end of said refill assembly is generally perpendicular to said body portion and has a tactile and shape configuration graspable by a person.

9. The nebulizer apparatus as in claim 7, wherein:

said body portion of said refill assembly has a first side wall defining a first air hole;

said body portion of said refill assembly has a second side wall defining a second air hole;

said flow member has a top wall defining an aperture adjacent said distal end thereof;

said first air hole and said aperture are aligned in fluid communication when said ramp member is at said first configuration;

said second air hole and said aperture are aligned in fluid communication when said ramp member is at said second configuration; and said aperture is not aligned with either said first air hole nor said second air hole when said ramp member is at said operational configuration.

10. The nebulizer apparatus as in claim 1, wherein:

said atomizer member has a tubular configuration defining an interior area having opposed closed ends, each closed end defining a channel connecting the interior area with ambient air outside said atomizer assembly;

said atomizer member includes a pair of baffles mounted externally to said opposed closed ends, respectively, of said atomizer member, said pair of baffles being positioned in alignment with said channels of said closed ends, respectively, and displaced therefrom, whereby the compressed airflow carrying the atomized first and second liquid medicines impacts said pair of baffles after passing through said channels, respectively.

11. A dual chamber nebulizer apparatus for atomizing a first and second liquid medicine and for administering the atomized medicine, comprising:
   a housing having a first chamber for holding the first liquid medicine and a second chamber for holding the second liquid medicine, said housing having a barrier wall that separates said first chamber from said second chamber;
   an atomizer member situated in an upper portion of said housing and configured to atomize liquid into vapor;
   a flow member coupled to said housing and in fluid communication with said atomizer member, said flow member having an inlet port selectively directing a compressed air flow to said atomizer member;
   a first aspiration tube having a proximal end in fluid communication with said atomizer member and a distal end extending into said first chamber, said first aspiration tube being perpendicular to said atomizer member;
   a second aspiration tube having a proximal end in fluid communication with said atomizer member and a distal end extending into said second chamber, said second aspiration tube being perpendicular to said atomizer member;
   wherein:
      said atomizer member, said flow member, and said first and second aspiration tubes collectively form a junction that is operable to draw the first and second liquid medicines from said first and second medicine chambers via said first and second aspiration tubes, respectively, into said atomizer member where the compressed air flow atomizes the first and second liquid medicines;
      said atomizer member has a tubular configuration defining an interior area having opposed closed ends, each closed end defining a channel connecting the interior area with ambient air outside said atomizer assembly;
      said atomizer member includes a pair of baffles mounted externally to said opposed closed ends, respectively, of said atomizer member, said pair of baffles being positioned in alignment with said channels of said closed ends, respectively, and displaced therefrom, whereby the compressed airflow carrying the atomized first and second liquid medicines impacts said pair of baffles after passing through said channels, respectively.

12. A dual chamber nebulizer apparatus for atomizing a first and second liquid medicine and for administering the atomized medicine, comprising:
   a housing having a first chamber for holding the first liquid medicine and a second chamber for holding the second liquid medicine, said housing having a barrier wall that separates said first chamber from said second chamber;
   an atomizer member situated in an upper portion of said housing that is configured to atomize liquid into vapor;
   a flow member coupled to said housing and in fluid communication with said atomizer member, said flow member having an inlet port selectively directing a compressed air flow to said atomizer member;
   a first aspiration tube having a proximal end in fluid communication with said atomizer member and a distal end extending into said first chamber, said first aspiration tube being perpendicular to said atomizer member;
   a second aspiration tube having a proximal end in fluid communication with said atomizer member and a distal end extending into said second chamber, said second aspiration tube being perpendicular to said atomizer member;
   wherein said atomizer member, said flow member, and said first and second aspiration tubes collectively form a junction that is operable to draw the first and second liquid medicines from said first and second medicine chambers via said first and second aspiration tubes, respectively, into said atomizer member where the compressed air flow atomizes the first and second liquid medicines;
   a delivery member having a proximal end coupled to an upper end of said housing and in fluid communication with said atomizer member for receiving said atomized first and second medicines and a distal end displaced from said housing;
   wherein said delivery member includes an outlet port situated at said distal end;
   a refill assembly having an inner end coupled to a distal end of said flow member and an outer end opposite said inner end and situated outside of said housing, said refill assembly including a body portion having a tubular configuration and extending between said inner and outer ends;
   wherein said delivery member is constructed of flexible tubing that is selectively shaped to extend away from said housing in any direction.

13. The nebulizer apparatus as in claim 12, wherein said delivery member is length adjustable.

14. The nebulizer apparatus as in claim 12, wherein said delivery member is constructed of flexible plastic tubing having a plurality of pleated coil sections.

15. The nebulizer apparatus as in claim 12, wherein:
   said refill assembly includes a ramp member coupled to said body portion of said ramp assembly, said ramp member having a planar configuration;
   said inner end of said refill assembly is rotatably coupled to said distal end of said flow member so that said refill member is rotatable between a first refill configuration allowing access only to said first chamber and a second refill configuration allowing access only to said second chamber and an operational configuration allowing access to both first and second chambers.

16. The nebulizer apparatus as in claim 15, wherein:
said ramp member covers an open top defined by said second chamber when said ramp member is at said first configuration and said ramp member covers an open top defined by said first chamber when said ramp member is at said second configuration.

17. The nebulizer apparatus as in claim 12, wherein:
said body portion of said refill assembly has a first side wall defining a first air hole;
said body portion of said refill assembly has a second side wall defining a second air hole;
said flow member has a top wall defining an aperture adjacent said distal end thereof;
said first air hole and said aperture are aligned in fluid communication when said ramp member is at said first configuration;
said second air hole and said aperture are aligned in fluid communication when said ramp member is at said second configuration; and
said aperture is not aligned with either said first air hole nor said second air hole when said ramp member is at said operational configuration.

18. The nebulizer apparatus as in claim 12, wherein:
said atomizer member has a tubular configuration defining an interior area having opposed closed ends, each closed end defining a channel connecting the interior area with ambient air outside said atomizer assembly;
said atomizer member includes a pair of baffles mounted externally to said opposed closed ends, respectively, of said atomizer member, said pair of baffles being positioned in alignment with said channels of said closed ends, respectively, and displaced therefrom, whereby the compressed airflow carrying the atomized first and second liquid medicines impacts said pair of baffles after passing through said channels, respectively.

* * * * *